US00PP29298P2

(12) United States Plant Patent
Scheys

(10) Patent No.: US PP29,298 P2
(45) Date of Patent: May 15, 2018

(54) ***HEUCHERA* PLANT NAMED 'RED SEA'**

(50) Latin Name: ***Heuchera* hybrid**
Varietal Denomination: Red Sea

(71) Applicant: Diederik Alexander Maria Scheys, Réty (FR)

(72) Inventor: Diederik Alexander Maria Scheys, Réty (FR)

( * ) Notice: Subject to any disclaimer, the term of this patent is extended or adjusted under 35 U.S.C. 154(b) by 0 days. days.

(21) Appl. No.: 15/330,007

(22) Filed: Jul. 25, 2016

(51) Int. Cl.
*A01H 5/12* (2018.01)

(52) U.S. Cl.
USPC ..... Plt./440

(58) Field of Classification Search
USPC ..... Plt./440
CPC . A01H 5/12; A01H 5/02; A01H 5/025; A01H 5/00
See application file for complete search history.

(56) References Cited

U.S. PATENT DOCUMENTS

PP21,880 P2 * 4/2011 Egger ..... Plt./440

OTHER PUBLICATIONS

New Plants and Flowers Three *Heuchera* varieties with 'unique' foliage 2015, retrieved on Aug. 14, 2017, retrieved from the Internet at http://www.newplantsandflowers.com/three-heuchera-varieties-with-unique-foliage/ 2 pp.*

* cited by examiner

*Primary Examiner* — June Hwu
(74) *Attorney, Agent, or Firm* — Penny J. Aguirre

(57) ABSTRACT

A new cultivar of hybrid *Heuchera* named 'Red Sea', characterized by its leaves that are red in color with wavy margins and a glossy surface, and its early flowering season that continues throughout the summer.

2 Drawing Sheets

Botanical classification: *Heuchera* hybrid.
Cultivar designation: 'Red Sea'.

BACKGROUND OF THE INVENTION

The present invention relates to a new and distinct cultivar of *Heuchera*, botanically of hybrid origin and known as a *Heuchera* 'Red Sea' and is hereinafter referred to by its cultivar name 'Red Sea'.

The new cultivar was discovered as a chance seedling by the Inventor in summer of 2008 in a field plot of *Heuchera* in Pellenberg, Belgium. The parents of the new cultivar are unknown, however *Heuchera* 'Blackout' (U.S. Plant Pat. No. 20,613) and an unnamed and unpatented plant of *Heuchera villosa* with reddish foliage are thought to be possible parents based on their proximity to the discovered seedling and the characteristics of the new cultivar.

Asexual propagation of the new cultivar was first accomplished by tissue culture using meristem tissue under the direction of the Inventor in Beervelde, Belgium in September of 2008. Asexual propagation of the new cultivar by tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Red Sea' as a new and unique cultivar of *Heuchera*.

1. 'Red Sea' exhibits leaves with wavy margins.
2. 'Red Sea' exhibits leaves that are red in color with a glossy surface.

3. 'Red Sea' exhibits an early flowering season that continues throughout the summer.

'Red Sea' can be most closely compared to its probable parents. The unnamed plant of *Heuchera villosa* differs from 'Red Sea' in having leaves that are less red in color, leaf surfaces that are matte, ruffled leaf margins and a flower season that is shorter and commences later. 'Blackout' differs from 'Red Sea' in having leaves that are blackish in color, a less vigorous growth habit, less orbicular shaped leaves and inflorescences that are less narrow and less straight in aspect. 'Red Sea' can be compared to the *Heuchera* cultivars 'Mahogany' (U.S. Plant Pat. No. 19,072) and 'Fire Chief' (U.S. Plant Pat. No. 21,880). Both are similar to 'Red Sea' in leaf shape and leaf color. 'Mahogany' differs from 'Red Sea' in having a shorter plant height, leaf margins that are less wavy, petioles that are less pubescent and inflorescences that are wider and less dense. 'Fire Chief' differs from 'Red Sea' in having a shorter plant height, a less vigorous growth habit, and inflorescences that are shorter with less flowers that are larger in size.

BRIEF DESCRIPTION OF THE DRAWINGS

The accompanying colored photographs illustrate the overall appearance and distinct characteristics of the new *Heuchera*. The photographs were taken of a plant 3 years in age as grown in an unheated greenhouse in a 7.5 liter container in Pellenberg, Belgium.

The photograph in FIG. 1 provides a side view of the plant habit and foliage coloration of 'Red Sea' in bloom.

Figure 1:
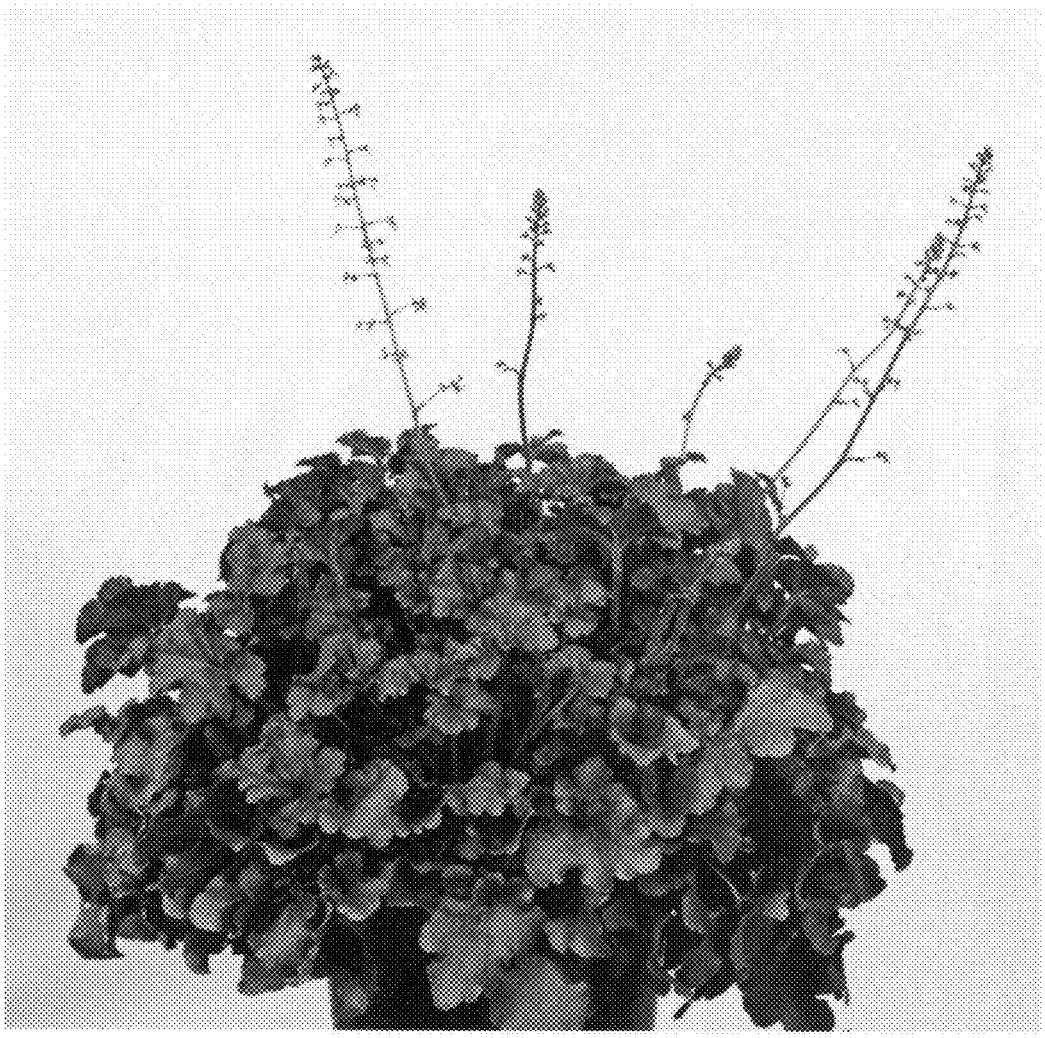
Figure 2:
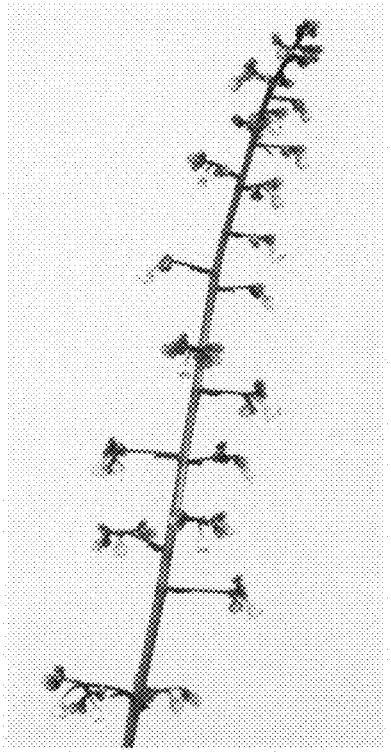

The photograph in FIG. 2 provides a close-up view of an inflorescence of 'Red Sea'.

Figure 3:
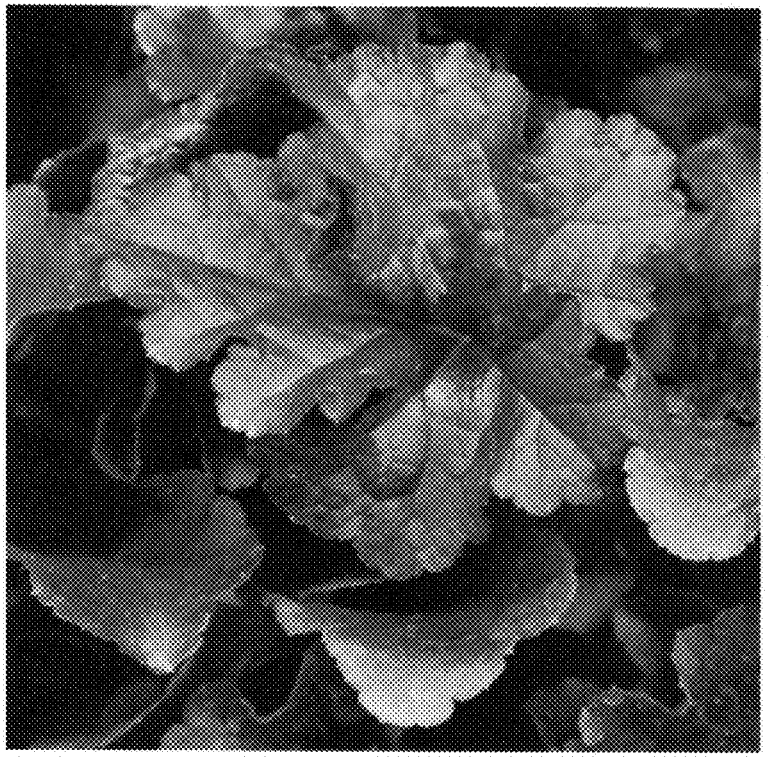

The photograph in FIG. 3 provides a close-up view of a leaf of 'Red Sea'.

The colors in the photographs are as close as possible with the digital photography techniques available, the color values cited in the detailed botanical description accurately describe the colors of the new *Heuchera*.

DETAILED BOTANICAL DESCRIPTION OF THE PLANT

The following is a detailed description of 3-year-old plants of the new cultivar as grown in an un-heated greenhouse in 7.5 liter containers in Pellenberg, Belgium. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Late spring through summer in Belgium.

*Plant type*.—Herbaceous perennial.

*Plant habit*.—Clump-forming, flattened globular, mounded foliage.

*Height and spread*.—An average of 26.1 cm in height to top of foliage and 100 cm in height to top of inflorescences and an average of 40 cm in width when grown in the landscape.

*Hardiness*.—At least in U.S.D.A. Zone 3 to 9.

*Diseases and pests*.—Not more susceptible to pests and diseases than other *Heuchera* varieties.

*Root description*.—Fibrous roots on woody rootstalks, 158D in color.

*Branching habit*.—Basal rosette, no lateral branches.

*Basal branching*.—No lateral stems only basal rosettes.

*Propagation*.—Tissue culture.

*Root development*.—An average of 13 weeks to fully develop from a tissue culture plug in a 7-cm or larger container.

*Growth rate*.—Moderately vigorous.

Foliage description:

*Leaf shape*.—Orbicular to broad ovate.

*Leaf division*.—Simple.

*Leaf base*.—Hastate, lobes moderately to strongly overlapping.

*Leaf apex*.—Obtuse.

*Leaf venation*.—Laciniate, upper surface color; 183B, lower surface color; 187D.

*Leaf margins*.—Lobed with an average of 5 lobes per leaf, wavy lobes with margins bi-crenate.

*Leaf attachment*.—Petiolate.

*Leaf arrangement*.—Alternate, basal rosettes.

*Leaf orientation*.—Typically nearly horizontal, wavy, and slightly cupped upwards.

*Leaf surface*.—Upper surface moderately glossy, lower surface glossy, both surfaces moderately pubescent with hairs an average of 1 mm in length and between NN155C and 156D in color.

*Leaf color*.—Young upper surface; 183A to 183B, young lower surface; 187C, mature upper surface; between 183B and 187A, fading during summer and fall to 177A, mature lower surface; 187B, fading during summer and fall to a color between N186D and N77B.

*Leaf size*.—Average of 9.2 cm in length and width.

*Leaf quantity*.—16 per basal rosette.

*Petioles*.—Round in shape, average of 14.7 cm in length and 3 mm in width, color; 187C to 187D, surface is moderately covered with short soft hairs.

*Stipules*.—Small leafy stipules at the base of each leaf, acute apex, with an average of 1.9 cm in length and 4 mm in width, lower surface color 187D, upper surface 64A, surface is moderately covered with short soft hairs.

Flower description:

*Inflorescence type*.—Compound spike.

*Inflorescence size*.—An average of 26.1 cm in height from the lowest flower to the top and 6 cm in width.

*Inflorescence number*.—An average of 20 compound spikes per 7.5 liter container.

*Flower fragrance*.—None.

*Flower quantity*.—Average of 165 per inflorescence.

*Flower lastingness*.—Average of one week, self cleaning.

*Flower buds*.—Broad ovate in shape, an average of 3 mm in diameter and 2 mm in length, 176D, tip tinged 152D in color.

*Flower aspect*.—Drooping to slightly outward.

*Flower type*.—Single, campanulate.

*Flower size*.—Average of 5.5 mm in diameter and 5 mm in depth.

*Petals*.—Average of 5, rotate arrangement and implanted in the hypanthium at base, oblanceolate in shape, margin is entire, apex is acute, upper and lower surface is matte and smooth, color when opening and fully upper and lower surface NN155D, 2.5 mm in length and 1 mm in width.

*Calyx*.—Campanulate, sepals fused to hypanthium, 3 mm in length and diameter.

*Sepals*.—5, fused into hypanthium, upper 35% free, elliptic in shape, 3 mm in length and 1 mm in width, margin is entire fused into hypanthium, upper 35% free, apex is obtuse, fused base, upper surface is matte, lower surface is moderately covered with very short glandular hairs an average of 0.3 mm in length and 157D, tips 183B in color, color; immature upper surface 152C, tinged 151B at the tips, immature lower surface; 176D, slightly tinged with 152D at apex, mature upper surface 152C, tinged 151B to 151C, mature lower surface 152C, tinged 151B to 151C and 176D.

*Peduncles*.—Moderate in strength, 3.5 mm in diameter, 50 cm in length, average angle of 70° to soil level, color ranging between 183A to 187B, surface densely covered with very short glandular hairs; 1 mm in length and a color between NN155C and 156D in color.

*Pedicels*.—Moderate in strength, average of 5 mm in length and 0.5 mm in diameter, average angle of 70°, 178A in color, surface densely covered with very short glandular hairs; 1 mm in length and a color between NN155C and 156D in color.

Reproductive organs:

*Gynoecium*.—Pistil; 2, stigma; pointed in shape, 4 mm in length, 31C to 31D in color, style; 1.6 mm in length, 27B to 27C in color, ovaries; superior and 27A in color.

*Androecium*.—Stamens; 5, anthers; ovate in shape, 0.5 mm in length and 23B in color, filament; 1.5 mm in length and NN155D in color, pollen is very low in quantity and to sparse to measure color.

*Seed/fruit*.—No fruit or seeds detected to date.

It is claimed:

1. A new and distinct cultivar of hybrid *Heuchera* plant named 'Red Sea' as herein illustrated and described.

* * * * *